(12) United States Patent
Kobayashi et al.

(10) Patent No.: US 9,791,869 B2
(45) Date of Patent: Oct. 17, 2017

(54) ENVIRONMENTAL CHAMBER CONTROL UNIT

(71) Applicant: NAGANO SCIENCE CO., LTD., Osaka (JP)

(72) Inventors: Yuichiro Kobayashi, Osaka (JP); Yuichi Sakamoto, Osaka (JP)

(73) Assignee: NAGANO SCIENCE CO., LTD., Osaka (JP)

( * ) Notice: Subject to any disclaimer, the term of this patent is extended or adjusted under 35 U.S.C. 154(b) by 581 days.

(21) Appl. No.: 14/446,835

(22) Filed: Jul. 30, 2014

(65) Prior Publication Data

US 2014/0339317 A1  Nov. 20, 2014

Related U.S. Application Data

(63) Continuation of application No. PCT/JP2012/007989, filed on Dec. 13, 2012.

(30) Foreign Application Priority Data

Feb. 3, 2012 (JP) ................................. 2012-022020

(51) Int. Cl.
*G01W 1/17* (2006.01)
*G05D 22/02* (2006.01)
(Continued)

(52) U.S. Cl.
CPC ............... *G05D 22/02* (2013.01); *F24F 3/14* (2013.01); *G01N 17/002* (2013.01); *G05D 23/19* (2013.01); *G01N 33/15* (2013.01)

(58) Field of Classification Search
None
See application file for complete search history.

(56) References Cited

U.S. PATENT DOCUMENTS

2002/0168293 A1  11/2002  Smith
2005/0285748 A1*  12/2005  Pedraza ................... E04B 1/70
340/602
(Continued)

FOREIGN PATENT DOCUMENTS

EP  2 351 972 A1  8/2011
JP  2002-364883  12/2002
(Continued)

OTHER PUBLICATIONS

Extended European Search Report for corresponding European Application No. 12867089.0 dated Aug. 10, 2015.
(Continued)

*Primary Examiner* — Lisa Caputo
*Assistant Examiner* — Nasir U Ahmed
(74) *Attorney, Agent, or Firm* — Renner Otto Boisselle & Sklar, LLP

(57) ABSTRACT

A control unit is added to the environmental tester including a thermostat-humidistat container, an air conditioner, a first temperature and humidity sensor for measuring temperature and humidity in the thermostat-humidistat container, a controller for receiving a first signal from the first temperature and humidity sensor to control the air conditioner. The control unit includes a second temperature and humidity sensor configured to measure the temperature and humidity distribution in the thermostat-humidistat container, and an additional unit configured to receive the first signal and set values for the temperature and the humidity from the controller, and receive a second signal from the second temperature and humidity sensor, compute a correction value from the received first signal, second signal, and set values, and send the correction value to the controller.

4 Claims, 4 Drawing Sheets

(51) Int. Cl.
    *G01N 17/00*     (2006.01)
    *F24F 3/14*     (2006.01)
    *G05D 23/19*     (2006.01)
    *G01N 33/15*     (2006.01)

(56) References Cited

U.S. PATENT DOCUMENTS

| | | | |
|---|---|---|---|
| 2009/0140060 A1* | 6/2009 | Stoner | G05D 23/1934 236/51 |
| 2011/0213501 A1* | 9/2011 | Jin | F24F 11/001 700/276 |

FOREIGN PATENT DOCUMENTS

| | | |
|---|---|---|
| JP | 2010-107062 | 5/2010 |
| JP | 2010-210443 | 9/2010 |
| WO | WO 2007/134621 A1 | 11/2007 |

OTHER PUBLICATIONS

International Search Report for corresponding International Application No. PCT/JP2012/007989 dated Feb. 12, 2013.
Form PCT/ISA/237 for corresponding International Application No. PCT/JP2012/007989 dated Feb. 12, 2013.

\* cited by examiner

ENVIRONMENTAL CHAMBER CONTROL UNIT

CROSS-REFERENCE TO RELATED APPLICATIONS

This is a continuation of International Application No. PCT/JP2012/007989 filed on Dec. 13, 2012, which claims priority to Japanese Patent Application No. 2012-022020 filed on Feb. 3, 2012. The entire disclosures of these applications are incorporated by reference herein.

BACKGROUND

The present disclosure relates to control unit capable of being added to, for example, thermostat-humidistat containers (chambers) and improving temperature and humidity distribution efficiency.

For example, an environmental tester such as a thermostat-humidistat container has been used for stability tests of pharmaceuticals, or the like in order to test the performance of a product under predetermined temperature and predetermined humidity. In such an environmental tester, a temperature sensor and a humidity sensor are provided in a thermostat-humidistat container surrounded by adiabatic walls, and an air conditioner including a refrigerator, a humidifier, and a heater is controlled based on values measured by these sensors, thereby allowing circulation of air between the thermostat-humidistat container and the air conditioner so that the temperature and the humidity in the thermostat-humidistat container are kept to target temperature and target humidity, respectively (see, for example, Japanese Unexamined Patent Publication No. H07-140061).

In conventional environmental testers, a temperature sensor and a humidity sensor for measuring the control physical quantities used to control the air conditioner are generally arranged near an outlet (or an inlet) of the conditioned air. This is because the temperature and the humidity measured near the outlet of the conditioned air can change quickly in response to the control of the air conditioner with a small lag, thereby allowing stable control of the air conditioner.

SUMMARY

However, in the conventional environmental tester, only a single measurement sensor for measuring the temperature and the humidity is provided near the outlet, or the like, so that only the temperature and the humidity near the measurement sensor are adjusted to preset target temperature and preset target humidity, respectively. Thus, the temperature and the humidity are not always adjusted to the target temperature and humidity in the entire part of the thermostat-humidistat container.

Therefore, in order to reduce deviations of the values of the temperature and the humidity measured by the measurement sensor from average values of the temperature distribution and the humidity distribution in the thermostat-humidistat container, it is effective to perform control such that the temperature and the humidity in the container are continuously measured to recognize the deviations of the temperature and the humidity measured by the sensor from the target temperature and the target humidity, respectively, and the deviations are corrected.

The configuration of an existing controller has to be modified in order to perform the control of correcting the deviations of the values measured by the measurement sensor from the average values of the temperature distribution and the humidity distribution in the thermostat-humidistat container. That is, the controller has to be replaced with a controller in which a circuit has been modified to receive signals from a sensor for measuring the temperature and humidity distributions and a control program has been modified to correct the deviations.

The replacement of the controller costs a lot and also requires that the environmental tester is stopped for a long period of time.

In one general aspect, the present disclosure describes a technique for improving the temperature and humidity distribution efficiency in the thermostat-humidistat container at low costs and with high accuracy.

The above general aspect may include a control unit having a configuration in which an additional sensor configured to measure distributions of temperature and humidity and an additional unit configured to receive a signal from the additional sensor and a signal from an existing temperature and humidity sensor, and compute deviations of the temperature and the humidity from set values for the temperature and the humidity are added to an existing environmental tester.

Specifically, a control unit according to the present disclosure is directed to a control unit to be added to an environmental tester including a thermostat-humidistat container defining a closed space, an air conditioner for controlling temperature and humidity in the thermostat-humidistat container, a first temperature and humidity sensor for measuring the temperature and the humidity in the thermostat-humidistat container, and a controller for receiving a first signal from the first temperature and humidity sensor and controlling the air conditioner. The control unit includes: a second temperature and humidity sensor configured to measure temperature and humidity distribution in the thermostat-humidistat container; and an additional unit configured to receive the first signal and set values for the temperature and the humidity from the controller, and a second signal from the second temperature and humidity sensor, compute a correction value from the received first and second signals and the received set values, and send the correction value to the controller.

The control unit of the present disclosure includes the additional unit configured to receive the first signal from the existing first temperature and humidity sensor and the set values, and receive a second signal from the added second sensor, compute a correction value from the signals and the set values, and send the computed correction value to the existing controller. That is, a correction value sent from the additional unit may only be added to an operating section of the existing controller, and thus the control of the temperature and the humidity in the thermostat-humidistat container can be used as it is. Thus, the temperature and humidity distribution efficiency in the thermostat-humidistat container can be improved at low costs and with high accuracy.

In the control unit of the present disclosure, the second temperature and humidity sensor may include a plurality of second temperature and humidity sensors arranged in the thermostat-humidistat container, and the additional unit may obtain the correction value by computing a difference between the first signal and a median of the plurality of second signals.

Moreover, in the control unit of the present disclosure, the first temperature and humidity sensor and each of the second temperature and humidity sensors are preferably equivalent to each other in accuracy.

The control unit according to the present disclosure can be used by being added to an existing controlling section of an environmental tester, so that the temperature and humidity distribution efficiency in the thermostat-humidistat container can be improved at low costs and with high accuracy.

DETAILED DESCRIPTION

Embodiments according to the present disclosure will be described with reference to the drawings. The following embodiments are merely a preferred example in nature, and are not intended to limit the scope, applications, and use of the disclosure.

(Embodiment)

Figure 1:
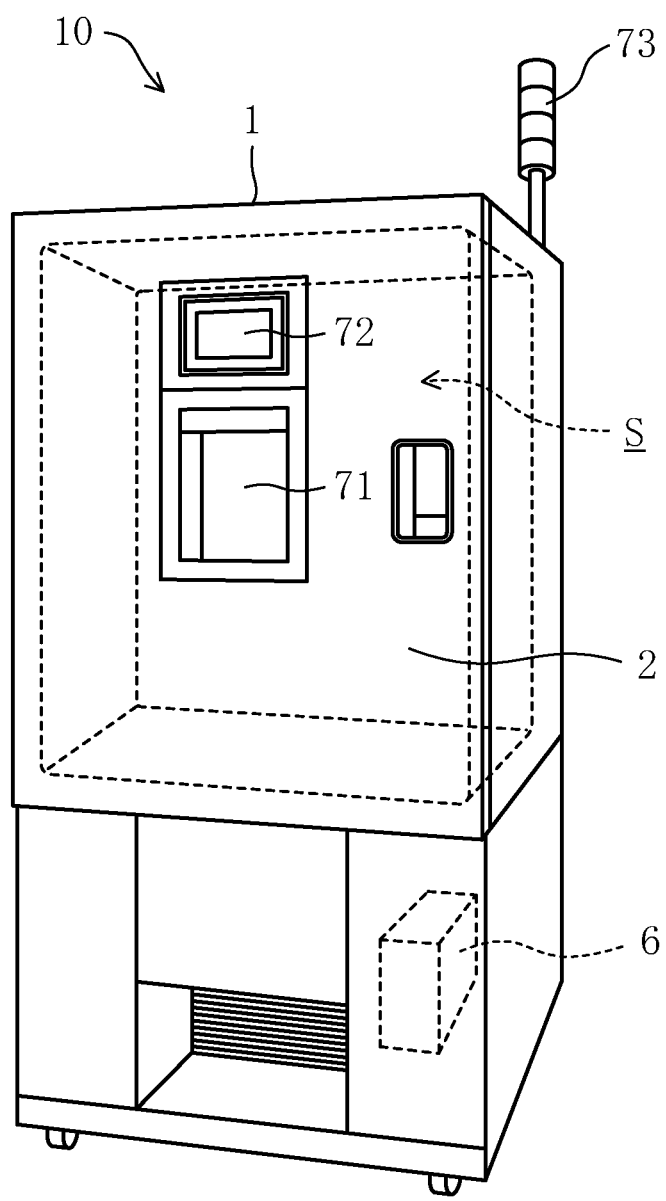
FIG. 1 is a perspective view illustrating a thermostat-humidistat container in an environmental tester according to an embodiment of the present disclosure.
Figure 2:
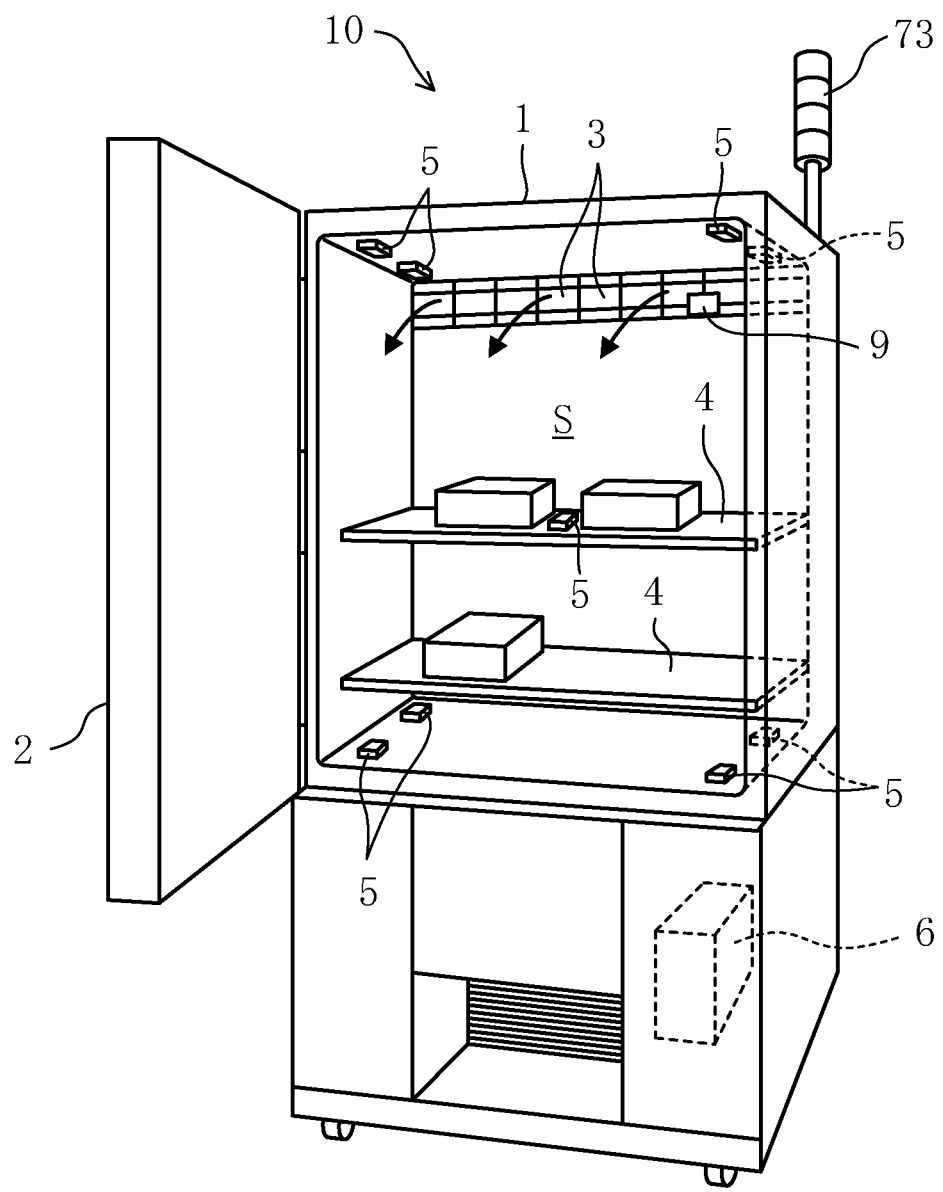
FIG. 2 is a perspective view illustrating the inside of a test chamber in the thermostat-humidistat container of the environmental tester according to the embodiment of the present disclosure.

FIGS. 1 and 2 show a thermostat-humidistat container 1 (chamber) as an environmental tester 10 according to an embodiment of the present disclosure. The thermostat-humidistat container 1 is used for stability tests of pharmaceuticals, for example. For this reason, temperature and humidity in a test chamber S are stably kept within the predetermined ranges, respectively.

As illustrated in FIG. 1, the thermostat-humidistat container 1 has a contour in the shape of a substantially rectangular parallelepiped, and a door 2 extending from an upper end to a center section of a front face of the thermostat-humidistat container 1 is attached to the thermostat-humidistat container 1 to be able to open and close. A consol panel 71 for, for example, setting target values for controlling temperature and humidity and a display 72 for displaying the set values, and the like are disposed to be aligned in the vertical direction on a front face of the door 2.

As illustrated in FIG. 2, the door 2 of the thermostat-humidistat container 1 is opened to access to the test chamber S which is in the shape of a substantially rectangular parallelepiped and is formed in the thermostat-humidistat container 1, so that a specimen can be placed in the test chamber S, or a specimen placed in the test chamber can be taken out. An air outlet 3 is formed in an upper portion of a wall surface at the depth of the test chamber S, and through the air outlet 3, conditioned air of adjusted temperature and humidity is discharged to the test chamber S from an air conditioner 8 (see FIG. 3) including a refrigerator, a humidifier, a heater, etc. An air inlet is formed in a lower portion of the wall surface at the depth of the test chamber S, and air in the test chamber S is sucked through the air inlet and is then supplied to the air conditioner 8. Thus, in the thermostat-humidistat container 1, air is circulated between the test chamber S and the air conditioner 8, thereby stably keeping the temperature and the humidity in the test chamber S within the predetermined ranges, respectively. The thermostat-humidistat container 1 defines a closed space between the test chamber S and the air conditioner 8.

In the present embodiment, a configuration in which the air outlet 3 is formed in the upper portion of the wall surface at the depth of the test chamber S, and the air inlet is formed in the lower portion of the wall surface has been described. However, this configuration is a mere example, and the positions of the air outlet and the air inlet can be suitably determined.

In the test chamber S, in the illustrated example, two shelf boards 4 are arranged to be aligned in the vertical direction, and specimens are placed on the shelf boards 4. The number and the position of the shelf board 4 are suitably determined.

Four additional sensors 5 are arranged respectively on a ceiling surface, and on a bottom surface of the test chamber S to have intervals therebetween, and a single additional sensor 5 is arranged at the center of the test chamber S (at the center of the shelf board 4 in the illustrated example). The nine additional sensors 5 in total are sensors for measuring the temperature and the humidity at the respective positions in the test chamber S to determining the temperature and humidity distribution in the thermostat-humidistat container. The number of the additional sensors 5 is not limited to nine, and the configuration shown in FIG. 2 is merely an example. The arrangement positions of the additional sensors 5 can suitably be determined depending on the number of the additional sensors 5. However, the additional sensors 5 are preferably placed substantially uniformly in the test chamber S to obtain the distributions of the temperature and the humidity in the test chamber S.

As described above, the additional sensors 5 are preferably placed at nine positions in total, i.e., at eight corners and the center of the test chamber S. However, the positions of the additional sensors 5 are not limited to the above nine positions. As long as the additional sensor 5 is arranged at at least one position away from an existing first temperature and humidity sensor 9 described below, the temperature and humidity distribution efficiency in the thermostat-humidistat container is improved compared to that in a configuration to which a control unit 65 of the present embodiment is not added.

The thermostat-humidistat container 1 includes a single first temperature and humidity sensor 9 arranged at the air outlet 3, and based on values measured by the first temperature and humidity sensor 9, the temperature, the relative humidity, and the absolute humidity of air discharged through the air outlet 3 are determined. The arrangement position of the first temperature and humidity sensor 9 is not limited to the position near the air outlet 3, but the first temperature and humidity sensor 9 may be arranged near the air inlet.

Measured signals from the first temperature and humidity sensor 9 is sent to a controller 6 disposed in a lower portion of the thermostat-humidistat container 1. The controller 6 controls the air conditioner 8 based on values measured by the sensors 5 and 9 in such a manner that the temperature and the humidity in the test chamber S are the predetermined temperature and humidity, respectively. In the present embodiment, measured signals from the additional sensors 5 are sent to an additional unit 60. These plurality of additional sensors 5 and the additional unit 60 form the control unit 65 according to the present embodiment.

Figure 3:
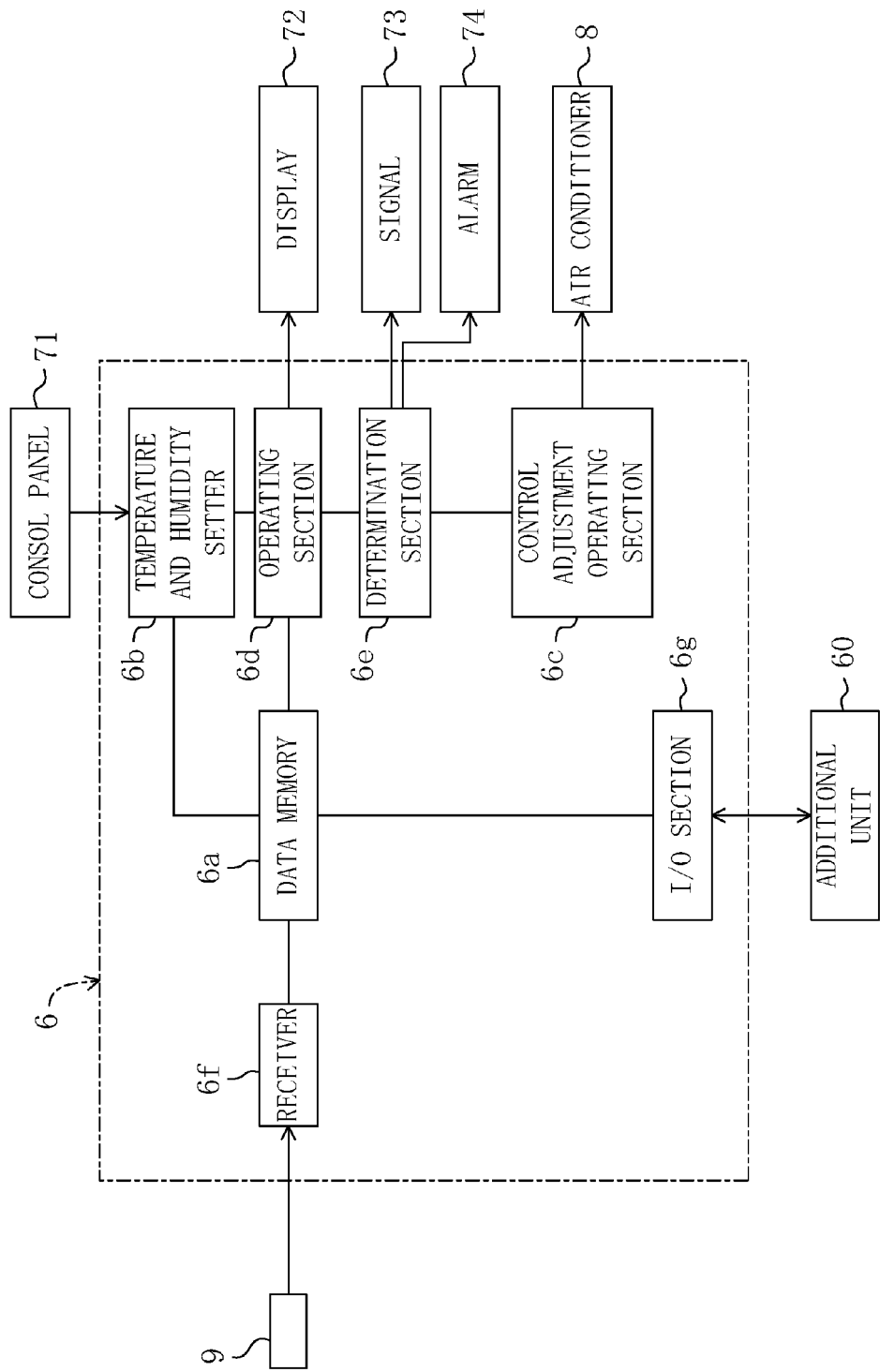
FIG. 3 is a functional block diagram illustrating a structure in the thermostat-humidistat container of the environmental tester according to the embodiment of the present disclosure.

As illustrated in FIG. 3, the controller 6 includes a receiver 6f configured to receive a signal from the first temperature and humidity sensor 9, and a data memory 6a configured to store the signal received by the receiver 6f.

The controller 6 further includes a temperature and humidity setter 6b for setting target values for controlling the temperature and the humidity in the test chamber S based on signals from the consol panel 71 through which an operator sets the target temperature and humidity, and an operating section 6d which receives signals from the temperature and humidity setter 6b and the data memory 6a, and carries out various operations for controlling the air conditioner 8 as described below. Where necessary, the results of the operations are shown on the display 72 provided on the door 2 of the thermostat-humidistat chamber 1.

The operating section 6d in the controller 6 computes the differences of the values of the temperature and the humidity measured by the first temperature and humidity sensor 9 from the set values, thereby generating a first correction value. The differences of the values measured by the first temperature and humidity sensor 9 from the set values are determined in a determination section 6e. Based on the determination results, a signal 73 and an alarm 74 which give an operating section a warning are operated.

In the present embodiment, as described later, the differences of the values of the temperature and the humidity measured by the first temperature and humidity sensor 9 from the set values are computed based on measured data from the first temperature and humidity sensor 9 and the plurality of additional sensors 5, and are generated as second correction values by the additional unit 60.

The controller 6 further includes a control adjustment operating section 6c which carries out an operation for control adjustments of the air conditioner 8. Based on the determination results of the determination section 6e and the second correction values generated by the additional unit 60, the control adjustment operating section 6c controls the air conditioner 8.

The controller 6 according to the present embodiment further includes an I/O section 6g for communication with the additional unit 60.

Figure 4:
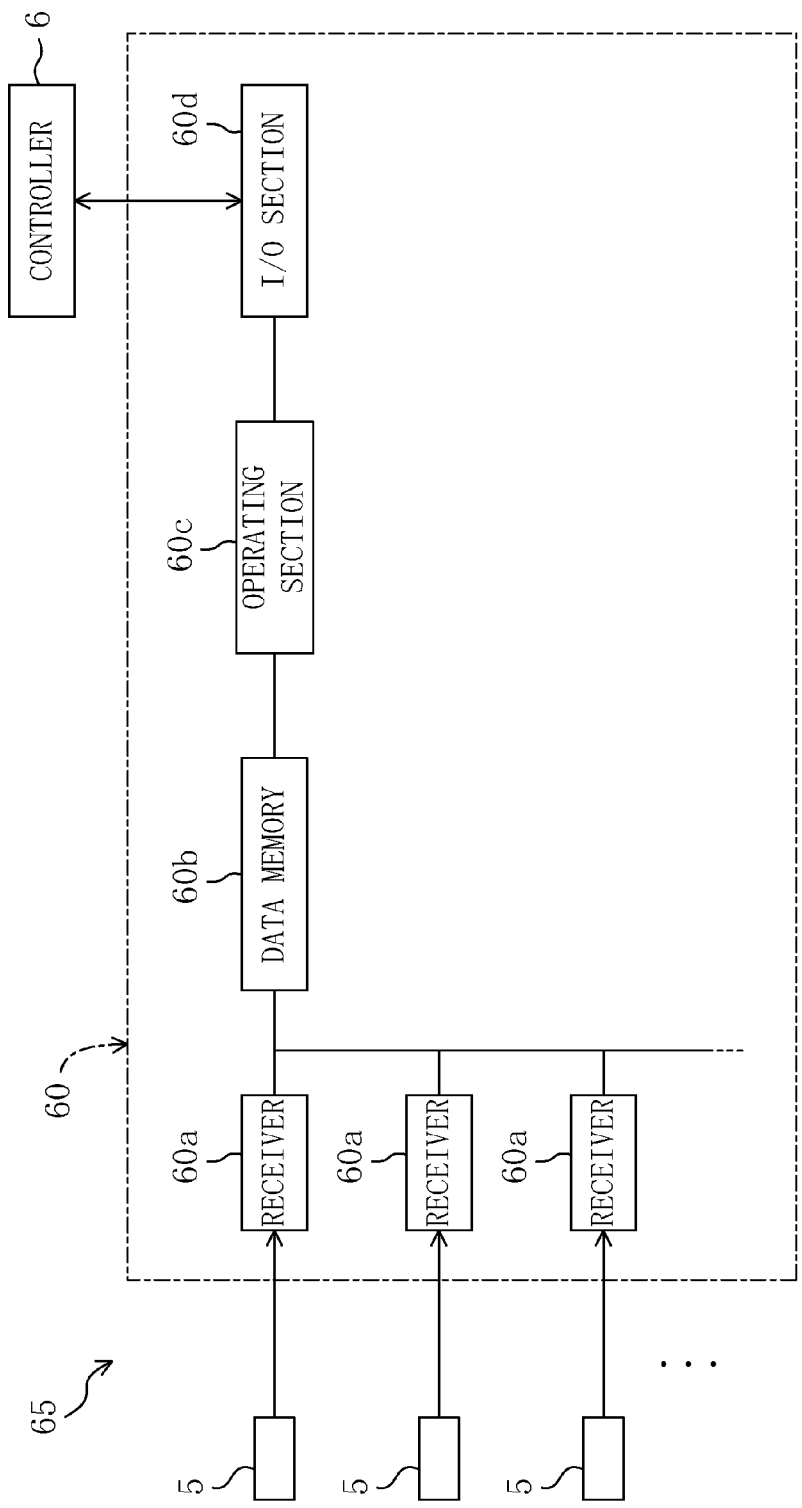
FIG. 4 is a functional block diagram illustrating a structure in a control unit added to the environmental tester of the embodiment of the present disclosure.

In contrast, the additional unit 60 according to the present embodiment includes, as illustrated in FIG. 4, receivers 60a configured to receive signals from the additional sensors 5, and a data memory 60b configured to store the signals received by the receivers 60a, the set values for the temperature and the humidity from the controller 6, and the values measured by the first temperature and humidity sensor 9.

The additional unit 60 further includes an operating section 60c configured to calculate the temperature and humidity distribution in the thermostat-humidistat container by an operation from the values measured by the first temperature and humidity sensor 9 and the values measured by the plurality of additional sensors 5, the values being stored in the data memory 60b. The results of the operation of the operating section 60c are sent to the controller 6 via an I/O section 60d.

(Operating Method)

Next, a method for operating the environmental tester 10 will be described. The door 2 of the thermostat-humidistat container 1 is opened to place a test specimen of the environmental test on the shelf board 4 disposed in the test chamber S.

Target values are input via the consol panel 71 disposed on the front face of the door 2. Here, an operator can see the target values displayed on the display 72 to check whether or not the operation is correct.

During operation of the environmental tester 10, conditioned air of adjusted temperature and humidity is discharged to the test chamber S by the air conditioner 8 through the air outlet 3. Air is supplied to the air conditioner 8 through the air inlet disposed in the lower portion of the wall surface at the depth in the test chamber S. The environmental tester 10 is operated such that while the air is circulated in this way between the test chamber S and the air conditioner 8, the conditioned air whose temperature and humidity has been adjusted in the air conditioner 8 is supplied to the test chamber S in such a manner that the temperature and the humidity in the test chamber S are the input target values.

Specifically, the set values for the temperature and the humidity input via the consol panel 71 are sent from the data memory 6a of the controller 6 via the I/O section 6g to the additional unit 60, for example, at the timing of the input of the set values.

As illustrated in FIG. 3, temperature and humidity data signals measured by the first temperature and humidity sensor 9 disposed near the air outlet 3 in the test chamber S are stored in the data memory 6a via the receiver 6f of the controller 6. Timing at which the data signals are stored in the data memory 6a occurs in a predetermined cycle. Concurrently with storing the data signals measured by the first temperature and humidity sensor 9 in the data memory 6a, the data signals measured by the first temperature and humidity sensor 9 are sent from the data memory 6a via the I/O section 6g to the additional unit 60.

On the other hand, temperature and humidity data signals measured by each of the nine additional sensors 5 substantially uniformly disposed in the test chamber S are stored in the data memory 60b via the receivers 60a of the additional unit 60. Timing at which the storing the temperature and humidity data signals are stored in the data memory 60b occurs preferably in the same cycle as that of the controller 6. However, the timing of sampling of the controller 6 and the timing of sampling of the additional unit 60 are not necessarily synchronous with each other.

The operating section 60c computes the deviations of data signals from the additional sensors 5 stored in the data memory 60b from the data signals from the first temperature and humidity sensor 9 stored in the data memory 60b. In this case, a median or an average value of the data signals from the additional sensors 5 may be used in place of data signals from the additional sensors 5.

The second correction values computed by the operating section 60c are sent to the controller 6 via the I/O section 60d.

The second correction values sent from the additional unit 60 are stored in a predetermined region of the data memory 6a in the controller 6. The temperature and humidity setter 6b, the operating section 6d, the determination section 6e, and the control adjustment operating section 6c perform existing processes based on the second correction values stored in the predetermined region of the data memory 6a, so that it is possible to improve the temperature and humidity distribution efficiency.

The results (the second correction values, etc.) of the operation of the additional unit 60 can be displayed on the display 72 as needed.

In many cases, the existing controller 6 has an external communication function such as the I/O section 6g. However, when the existing controller 6 does not have the external communication function, the external communication function has to be provided to the controller 6.

The controller 6 has to update a control program (software) so as to be able to perform the process of storing the correction value computed by the additional unit 60 in the predetermined region of the data memory 6a, the process of reading the correction value from the predetermined region, etc.

As described above, according to the present embodiment, the existing controller 6 of the environmental tester 10 is used for controlling the temperature and the humidity, the control unit 65 according to the present disclosure, that is, the plurality of additional sensors 5 and the additional unit 60 is added by so-called retrofitting, so that it is possible to improve the temperature and humidity distribution efficiency in the thermostat-humidistat container.

Therefore, it is not necessary to replace the environmental tester 10, and thus, it is possible to improve the temperature and humidity distribution efficiency in the thermostat-humidistat container at low costs.

Since the control function of the existing controller 6 itself is used as it is, the control unit 65 according to the present embodiment can be added to the existing environmental tester 10 even when the manufacturer of the control unit 65 is different from the manufacturer of the environmental tester 10 to which the control unit 65 is added.

<<Other Embodiments>>

The embodiment may have the following configuration.

In the present embodiment, a configuration in which the thermostat-humidistat container 11 includes the test chamber S provided therein has been described. However, the size of the test chamber S is not particularly limited. That is, a configuration in which a thermostat-humidistat room includes a test chamber S as a room having a size allowing the entrance of workers is also within the scope of the disclosure.

The present disclosure can be utilized in environmental testers including thermostat-humidistat containers, and is also widely applicable to domestic and industrial air conditioners.

What is claimed is:

1. A control unit for adding to an environmental chamber, the chamber comprising:
    a thermostat-humidistat container configured to define a closed space;
    an air conditioner configured to control temperature and humidity in the thermostat-humidistat container;
    a first temperature and humidity sensor configured to measure the temperature and the humidity inside the thermostat-humidistat container; and
    a controller having predetermined set values for temperature and humidity, and configured to receive a first signal from the first temperature and humidity sensor and to control the air conditioner based on the first signal and the predetermined set values; wherein
    the control unit includes:
    a second temperature and humidity sensor placed in different location with the first temperature and humidity sensor inside the thermostat-humidistat container, and configured to measure temperature and humidity inside the thermostat-humidistat container; and
    an additional unit configured to receive the first signal and the predetermined set values from the controller, and a second signal from the second temperature and humidity sensor, and to compute a correction value based on the received first and second signals, and the received predetermined setting values, and to send the correction value to the controller.

2. The control unit according to claim 1, wherein
the second temperature and humidity sensor is configured to have a plurality of second temperature and humidity sensors placed inside the thermostat-humidistat container, and
the additional unit is configured to compute the correction value based on a difference between the first signal and a median of the second signals.

3. The control unit according to claim 2, wherein
the first temperature and humidity sensor and each of the second temperature and humidity sensors are equivalent to each other in accuracy.

4. The control unit according to claim 1, wherein
the first temperature and humidity sensor and the second temperature and humidity sensors are equivalent in accuracy.

* * * * *